(12) United States Patent
Yan et al.

(10) Patent No.: US 9,695,400 B2
(45) Date of Patent: Jul. 4, 2017

(54) HOMOZYGOUS AND HETEROZYGOUS IDH1 GENE-DEFECTIVE HUMAN ASTROCYTOMA CELL LINES

(75) Inventors: Hai Yan, Chapel Hill, NC (US); Darell Bigner, Mebane, NC (US); Genglin Jin, Chapel Hill, NC (US)

(73) Assignee: Duke University, Durham, NC (US)

( * ) Notice: Subject to any disclaimer, the term of this patent is extended or adjusted under 35 U.S.C. 154(b) by 34 days.

(21) Appl. No.: 13/878,596

(22) PCT Filed: Oct. 24, 2011

(86) PCT No.: PCT/US2011/057466
§ 371 (c)(1),
(2), (4) Date: Jun. 11, 2013

(87) PCT Pub. No.: WO2012/054915
PCT Pub. Date: Apr. 26, 2012

(65) Prior Publication Data
US 2013/0252330 A1    Sep. 26, 2013

Related U.S. Application Data

(60) Provisional application No. 61/405,873, filed on Oct. 22, 2010.

(51) Int. Cl.
*C12N 5/00*    (2006.01)
*C12N 5/09*    (2010.01)

(52) U.S. Cl.
CPC ................. *C12N 5/0693* (2013.01)

(58) Field of Classification Search
CPC .................................................. C12N 5/0693
USPC ........................................................ 435/325
See application file for complete search history.

(56) References Cited

FOREIGN PATENT DOCUMENTS

WO    2010028099 A1    3/2010

OTHER PUBLICATIONS

Watanabe et al., (2009, Am. J. Path., vol. 174(4), pp. 1149-1153).*
Capper et al., (2010, Brain Pathology, vol. 20, pp. 245-254, e-published Oct. 27, 2009).*
Paschka et al., (2008, J. Clin. Oncol., vol. 28, pp. 3636-3643).*
Luchman et al., (2013, Neuro-Oncology, vol. 15(8), pp. 979-980).*
Lovejoy et al. (2012. PLoS Genetics, vol. 8(7), pp. 1-16).*
Gupta et al. (2013, Modern Pathology, vol. 26, pp. 619-625).*
Galderisi et al. (2006, Cell Death and Differentiation, vol. 13, pp. 5-11).*
Hartmann et al. (2009, Acta Neuropathol, vol. 118, pp. 469-474).*
Arai et al. (1991, In Vitro Cell Dev. Biol. vol. 27A, pp. 606-614).*
Camelo-Piragua et al. (Apr. 2010, Acta Neuropathol, vol. 119, pp. 509-511).*
Dang et al. (2009, Nature, vol. 462, pp. 1-18).*
Pollard et al. (2009, Cell Stem Cell, vol. 4, pp. 568-580).*
Watanabe, T., et al., "IDH1 Mutations Are Early Events in the Development of Astrocytomas and Oligodendrogliomas," The American Journal of Pathology, vol. 174, No. 4, pp. 1149-1153, (Apr. 4, 2009).
Camelo-Piragua, S., et al., Mutant IDH1-specific immunohistochemistry distinguishes diffuse astrocytoma from astrocytosis, Acta Nueropathologica, vol. 119, pp. 509-511, (Jan. 1, 2010).
Kato, Y., et al., "A monoclonal antibody IMab-1 specifically recognizes IDH1 R132H, the most common glioma-derived mutation," Biochemical and Biophysical Research Communications, vol. 390 pp. 547-551, (Oct. 7, 2009).
Capper, D., et al., "Monoclonal antibody specific for IDH1 R132H mutation," Acta Neuropathol, vol. 118, pp. 599-601, (Oct. 2, 2009).
Sellner, L., et al., "Increased levels of 2-hydroxyglutarate in AML patients with IDH1-R132H and IDH2-R140Q mutations," European Journal of Haematology, vol. 85, pp. 457-459 (Jul. 26, 2010).
International Search Report Issued May 7, 2012 in PCT/US11/057466 Filed Oct. 24, 2011.

* cited by examiner

*Primary Examiner* — Thaian N Ton
*Assistant Examiner* — David A Montanari
(74) *Attorney, Agent, or Firm* — Banner & Witcoff, Ltd.

(57) ABSTRACT

We provide IDH1 gene-defective cell lines (e.g., IDH1R132H heterozygous and IDH1R132H homozygous) derived from dissociated human astrocytoma samples. The cells can be used alone or in combination with each other or other cell types as a tool for determining the impact of IDH1R132H on cellular biology, tumorigenesis, and metabolic profiles. The cell lines may be used to test and identify therapeutic targets and to screen for molecular therapeutic agents.

8 Claims, 7 Drawing Sheets

HOMOZYGOUS AND HETEROZYGOUS IDH1 GENE-DEFECTIVE HUMAN ASTROCYTOMA CELL LINES

This invention was made using funds from the U.S. National Institutes of Health, grant number R01CA140316. The U.S. government retains certain rights in the invention under the terms of the grant.

BACKGROUND OF THE INVENTION

Infiltration of the central nervous system by neoplastic cells in patients with glioblastoma multiforme (GBM) leads to neurological dysfunction and eventually to death. Gliomas contain specific histologic subtypes, the most common of which are astrocytomas, oligodendrogliomas, and ependymomas. They are a highly invasive, rapidly spreading form of brain cancer that is resistant to surgical and medical treatment. These tumors have been classified as grade I to grade IV on the basis of histopathological and clinical criteria established by the World Health Organization (WHO) (Louis, D. N. et al. (2007) Acta Neuropathol. 114:97). Generally, WHO grade I gliomas, considered to be benign, are often curable with complete surgical resection and rarely, if ever, evolve into higher grade lesions (Burger, P. C. et al. (eds.) (2000) Pathology and Genetics of Tumours of the Nervous System. IARC Press, Lyon pp. 45-51). In contrast, gliomas of WHO grade II or III are invasive, progress to higher-grade lesions, and have a poor outcome. Despite advances in surgical techniques, radiation therapy and adjuvant chemotherapy, WHO grade IV tumors (glioblastomas), which are the most invasive form, have a very poor prognosis (Strupp, R. et al. (2005) N. Engl. J. Med. 352:987; Wen, P. Y. et al. (2008) N. Engl. J. Med. 359:492).

Isocitrate dehydrogenase (IDH) is an enzyme that catalyzes the oxidative decarboxylation of isocitrate (ICT) to produce $\alpha$-ketoglutarate ($\alpha$KG). The activity of IDH is dependent on either nicotinamide adenine dinucleotide phosphate (NADP+-dependent IDH1 and IDH2) or nicotinamide adenine dinucleotide (NAD+-dependent IDH3). An unbiased, genome-wide analysis of the somatic mutations occurring in GBMs revealed recurrent mutations in R132, the active site of IDH1, a gene with no known link to gliomas, in 12% of tumors analyzed (see, e.g., Parsons, D. W. et al. (2008) Science 321:1807). Intriguingly, mutations of IDH1 predominantly occurred in younger patients, were associated with a better prognosis, and were preferentially found in tumors that possessed TP53 mutations but lacked other common GBM alterations: all characteristics of secondary GBMs. Additional studies have confirmed that IDH1 is mutated in >80% of secondary GBMs, whereas <10% of primary GBMs harbor these alterations (see, e.g., Balass, J. et al. (2008) Acta. Neuropathol. 597:602; Bleeker, F. E. et al. (2009) Hum. Mutat. 30:7; Yan, H. et al. (2009) N. Engl. J. Med. 360:765; Ichimura, K. et al. (2009) Neurooncol. 11:341; Kang, M. R. et al. (2009) Int. J. Cancer 125:353; Watanabe, T. et al. (2009) Am. J. Pathol. 174:1149). Mutations were recently identified that affected amino acid 132 of IDH1 in more than 70% of WHO grade II and III astrocytomas and oligodendrogliomas and in glioblastomas that developed from these low grade lesions. IDH1 and IDH2 mutations are also present in 23% of acute myeloid leukemia, but are rarely observed in other types of cancers, suggesting that IDH1 mutant dependent on specific cell type or cell environment. By far, the most common mutation seen in glioma patients is IDH1R132H.

In the past, researchers have had to rely on primary cultures of astrocytoma cells for cancer research. Such cultures have been of limited value, however, for the following reasons: (1) human astrocytoma cells are difficult to obtain; (2) very small numbers of cells can be obtained and cultured; and (3) the cultures can be maintained for short periods of time and die quickly. The establishment of an IDH1-mutated human astrocytoma cell line is therefore of significant value as it obviates the need for using primary cultures and enables scientists to perform studies that would not have been possible using primary cultures. Such a cell line would have utility for studies including those aimed at (1) determining the function of the IDH1 gene in human glioma cells; (2) studying gene-gene interactions, in order to elucidate the molecular mechanisms involved in tumorigenesis and molecules that may be drug targets; (3) identifying genes whose expression is altered as a consequence of IDH1 inactivation and this alteration, in order to identify those genes that determine the time of onset and severity of disease in different individuals; (4) making xenografts for in vivo animal models; and (5) screening for therapeutic agents that are effective in killing, or reducing/inhibiting the growth of the cells.

SUMMARY OF THE INVENTION

One aspect of the invention is an isolated and purified human astrocytoma cell which can grow indefinitely in culture and which comprises an IDH1 R132H allele and a wild-type IDH1 allele.

Another aspect of the invention are isolated and purified human astrocytoma cells which can grow indefinitely in culture and which comprise an IDH1 R132H allele and comprise no wild-type IDH1 alleles.

Still another aspect of the invention is an isolated and purified human astrocytoma cell which can grow indefinitely in culture and which comprises one wild-type IDH1 allele and no mutant IDH1 allele.

A further aspect of the invention is a set of isogenic human astrocytoma cell lines comprising at least two cell lines having a genotype selected from the group consisting of:

IDH1 R132H/IDH1 wild-type;
IDH1 R132H/IDH1 insertion mutation; and
IDH1 R132H deletion mutation/IDH1 wild type.

Another aspect of the invention is a kit comprising in a divided container or multiple containers cells of one or more cell line described above with regard to its IDH1 genotype or phenotype.

Still another aspect of the invention is a human xenograft made by transplanting any of the cells described into a different species under conditions so that the cells of the cell lines form tumors.

These and other embodiments provide the art with cell lines which can be used for screening potential anti-tumor agents.

DETAILED DESCRIPTION

Figure 1:
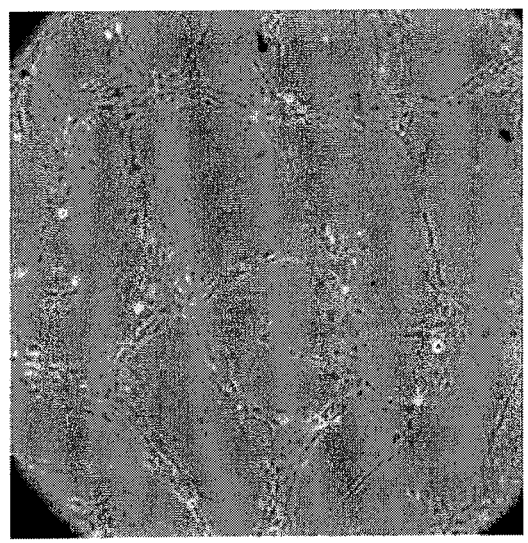
FIG. 1 is an image showing cell morphology of TB096-0096 (IDH1R132H heterozygous) cells. Image is at 100×.

The inventor have established and characterized stable, long-term human astrocytoma cell lines that are homozygous or heterozygous for mutations in the IDH1 gene. The established cell lines provide reagents for studying tumor growth and the biological effects of IDH1. The cell lines are useful tools to test different therapeutic approaches, e.g., chemotherapeutic, radiological, nutritional, alternative, or biological, in a relevant disease model. The cell lines can be used for studies in cell culture or can be transplanted into a laboratory animal, such as a nude mouse, to form a xenograft. Xenografts can be tested in vivo in the animal, or they can be removed and tested in vitro.

In order to study directly the effect of IDH1 gene mutations in human cancer cells the inventor(s) have generated cell lines having various IDH1 status (e.g., wild-type, IDH1R132H heterozygous, and IDH1R132H homozygous) from dissociated primary human astrocytoma samples. These cell lines can be used as a tool for determining the impact of IDH1R132H on cellular biology, tumorigenesis, and metabolic profiles. Moreover, these cell lines can be used for the testing of therapeutic targets and for the screening of molecular therapeutic agents.

Any means known in the art to generate a cell line which comprises a defective IDH1 gene can be used to obtain the IDH1 gene-defective cells. For example, an astrocytoma cell line can be used to give rise to an isogenic IDH1 negative cell line by promoterless homologous recombination (see, e.g., Waldman, T. et al. (1995) *Cancer Res.* 55:5187-5190, the contents of which are expressly incorporated by reference). Alternatively, as described below, a primary astrocytoma cell can be used which already has an IDH1 R132H mutation. A cell with two wild-type alleles of the IDH1 gene is a gene-normal cell, for purposes of the present disclosure. A cell with one or two mutant IDH1 alleles is termed an IDH1 gene-defective cell. Preferably, the IDH1 gene-normal cell used in the assay is the same type of cell (i.e., organ source) as the IDH1 gene-defective cell. More preferably, the two cell lines are isogenic or as closely isogenic as possible.

Any of the IDH1 alleles may be engineered to be present in a cell with any of the other alleles. Any of the alleles may be present in the heterozygous, homozygous, or hemizygous state. The presence of combinations of different alleles in a single cell may modify the phenotype.

Viability and cell death can be used as ways of assessing the effects of test agents on cells. Preferably a differential effect will be observed on an IDH1 gene-normal cell and an IDH1 gene-defective cell. Any assay for such effects can be used. In whole animals, regression of tumors can be observed. Alternatively, disease-free progression can be observed. Optionally, a change in survival can be observed. It is well known in the art that viability of a cell in culture can be determined by contacting the cell with a dye and viewing it under a microscope. Viable cells can be observed to have an intact membrane and do not stain, whereas dying or dead cells having "leaky" membranes do stain. Incorporation of the dye by the cell indicates the death of the cell. The most common dye used in the art for this purpose is trypan blue. Viability of cells can also be determined by detecting DNA synthesis. Cells can be cultured in cell medium with labeled nucleotides, e.g., $^3$H-Thymidine. The uptake or incorporation of the labeled nucleotides indicates DNA synthesis. In addition, colonies formed by cells cultured in medium indicate cell growth and is another way to test viability of the cells.

Apoptosis is a specific mode of cell death recognized by a characteristic pattern of morphological, biochemical, and molecular changes. Cells going through apoptosis appear shrunken, and rounded; they also can be observed to become detached from culture dish. The morphological changes involve a characteristic pattern of condensation of chromatin and cytoplasm which can be readily identified by microscopy. When stained with a DNA-binding dye, e.g., H33258, apoptotic cells display classic condensed and punctate nuclei instead of homogeneous and round nuclei.

A hallmark of apoptosis is endonucleolysis, a molecular change in which nuclear DNA is initially degraded at the linker sections of nucleosomes to give rise to fragments equivalent to single and multiple nucleosomes. When these DNA fragments are subjected to gel electrophoresis, they reveal a series of DNA bands which are positioned approximately equally distant from each other on the gel. The size difference between the two bands next to each other is about the length of one nucleosome, i.e., 120 base pair. This characteristic display of the DNA bands is called a DNA ladder and it indicates apoptosis of the cell. Apoptotic cells can be identified by flow cytometric methods based on measurement of cellular DNA content, increased sensitivity of DNA to denaturation, or altered light scattering properties. These methods are well known in the art and are within the scope of the present disclosure.

Abnormal DNA breaks are also characteristic of apoptosis and can be detected by any means known in the art. In one preferred embodiment, DNA breaks are labeled with biotinylated dUTP (b-dUTP). Cells are fixed and incubated in the presence of biotinylated dUTP with either exogenous terminal transferase (terminal DNA transferase assay; TdT assay) or DNA polymerase (nick translation assay; NT assay). The biotinylated dUTP is incorporated into the chromosome at the places where abnormal DNA breaks are repaired, and are detected with fluorescein conjugated to avidin under fluorescence microscopy.

Kits for screening various agents, e.g., chemotherapeutic agents, test compounds, anti-tumor agents and the like and for any other use described here, are easily assembled. Kits may comprise, consist of, or consist essentially of (1) a divided or undivided container(s) containing the cell line(s) of the present disclosure; (2) media for propagating cells, and (3) reagents and/or apparatus for detecting morphological, physiological and/or genetic responses of the cell lines, including cell viability. Other components routinely found in such kits may also be included together with instructions for use.

The use of "including," "comprising," "having," "containing," "involving," and variations thereof herein, is meant to encompass the items listed thereafter and equivalents thereof as well as additional items. For the purposes of promoting an understanding of the principles of the present disclosure, reference will now be made to preferred embodiments and specific language will be used to describe the same.

The articles "a" and "an" are used herein to refer to one or to more than one (i.e. at least one) of the grammatical object of the article. By way of example, "an element" means at least one element and can include more than one element.

Isolated and purified cells are the result of repeating cell culturing and passaging. Single cell culturing may be used. The repeated passages leads to a population which is considered purified, i.e., homogeneous in terms of genotype and cell type.

While the following terms are believed to be well understood by one of ordinary skill in the art, the following definitions are set forth to facilitate explanation of the presently disclosed subject matter. Although any methods, devices, and materials similar or equivalent to those described herein can be used in the practice or testing of the presently disclosed subject matter, representative methods, devices and materials are described.

The term "cell line," as used herein, refers to individual cells, harvested cells, and cultures containing the cells, so long as they are derived from cells of the cell line referred to. A cell line is said to be "continuous," "immortal," or "stable" if the line remains viable over a prolonged time, typically at least about six (6) months. Preferably, the cells remain viable for at least 40 passages. Such cell lines are said to grow indefinitely in culture.

A cell line is said to be "malignant" or "tumorigenic" if, when the cell line is injected into a host animal, the animal develops tumors or cancers that are anaplastic, invasive, and/or metastatic. A "human" tumor is comprised of cells that have human chromosomes. Such tumors include those in a human patient, and tumors resulting from the introduction of a human malignant cell line into a non-human host animal for at least about one week, one month, or several months.

The following examples are provided for exemplification purposes only and are not intended to limit the scope of the disclosure which has been described in broad terms above.

EXAMPLES

Example 1: Generation of T13096-0096 (IDH1R132 Heterozygous) Cell Line

Figure 2:
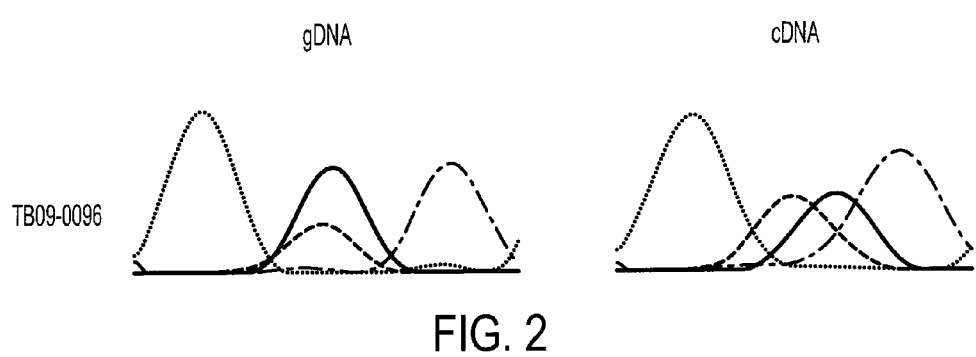
FIG. 2 shows sequencing analysis of TB096-0096 (IDH1R132H heterozygous). Representative sequencing chromatograms for IDH1 codon 132 in genomic DNA and cDNA. Wild-type allele (CGT) and mutant allele (CAT) code for an Arginine (R) or Histidine (H) at position 132.
Figure 3:
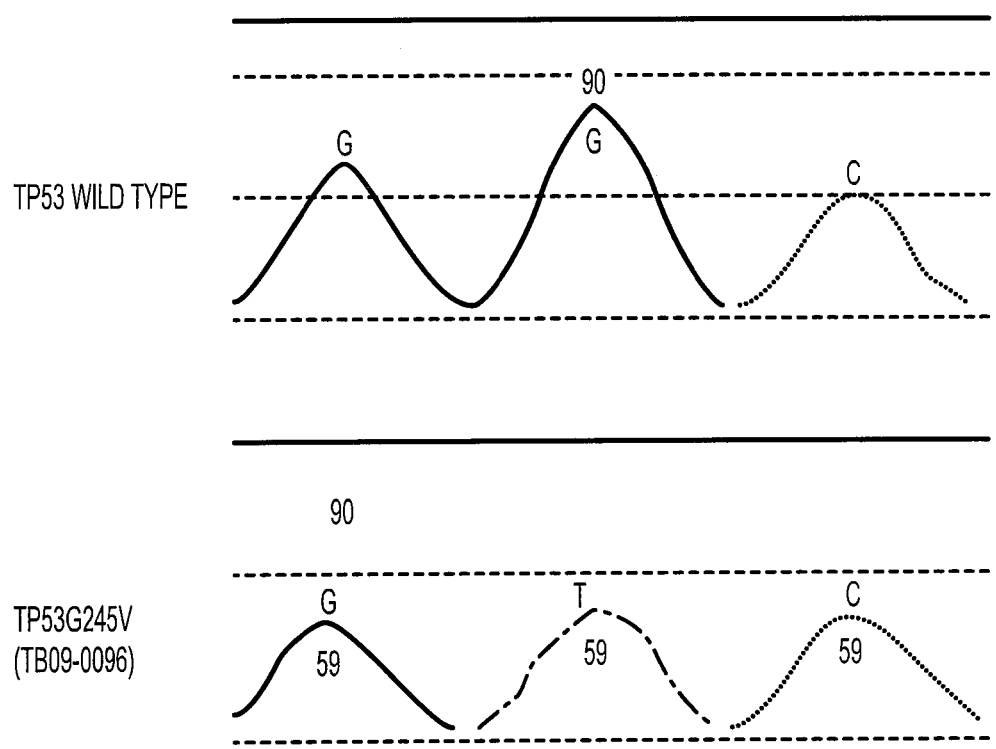
FIG. 3 shows representative sequencing chromatograms for TP53 codon 245 in genomic DNA of TB09-0096 (IDH1R132H heterozygous). TB09-0096 contains a homozygous TP53 mutation, with Gly (GGC) changed to Val (GTC) at position 245.
Figure 4:
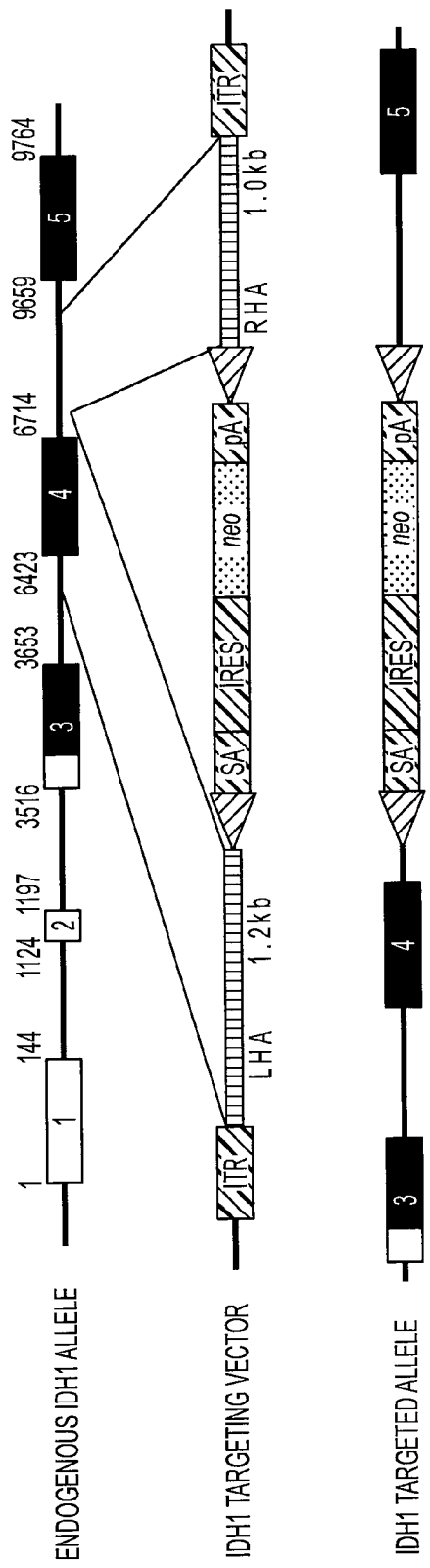
FIG. 4 depicts a strategy for making an insertion in the IDH1 allele in TB09-0096. Homology arms (HA) were cloned from TB09-0096 parent cells and are shown in red. The homology arms flank a synthetic exon promoter trap (SEPT) cassette. The promotorless SEPT element contains a splice acceptor (SA), internal ribosomal entry sequence (IRES), neomycin selectable marker (neo), and polyadenylation site (pA) which are flanked by LoxP sites (green triangles). Inverted terminal repeats (ITR) of the adeno-associated virus (AAV) vector flank the homology arms.
Figure 5:
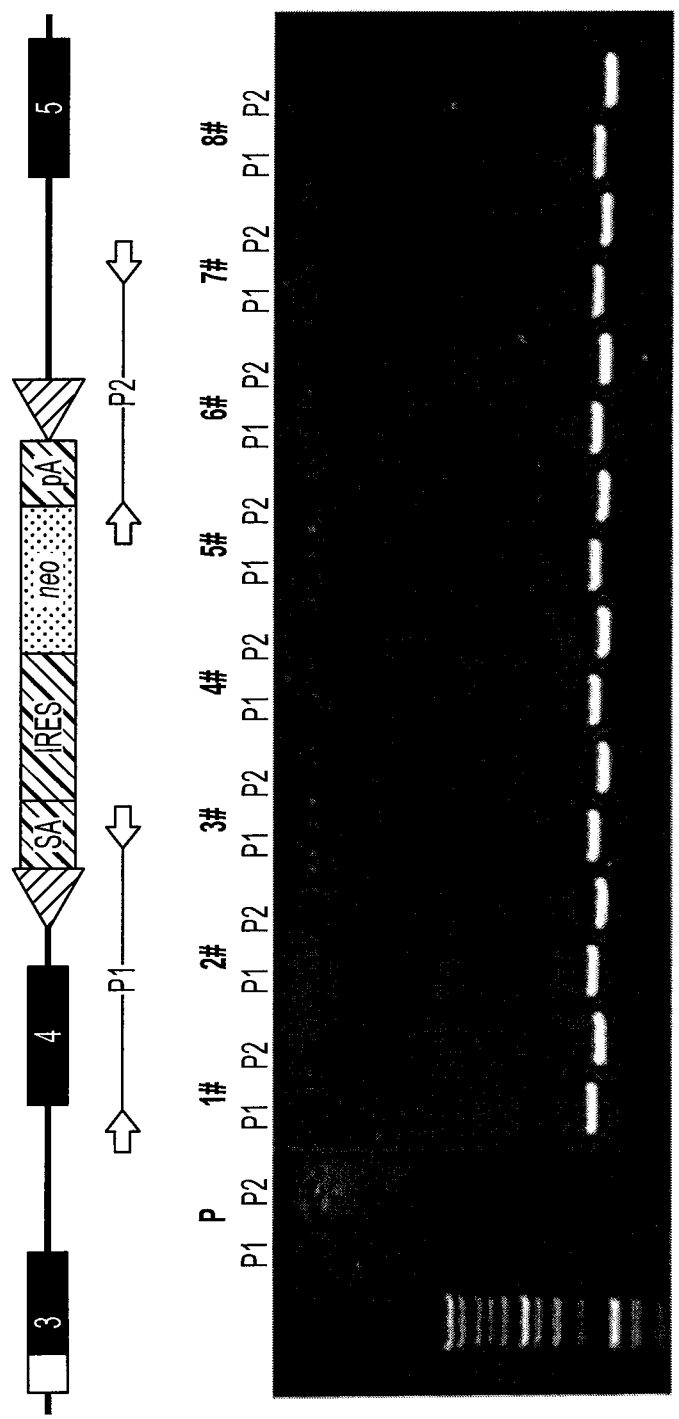
FIG. 5 shows a PCR screen for homologous integration. PCR primer pairs are indicated as P1-P2. The screening approach employs one primer that anneals within the SEPT element and a second primer that is outside the homology region. Two primer sets confirm homologous integration for clones #1, #2, #3, #4, #5, #6, #7 and #8, but not for parent (P) TB09-0096 cells.
Figure 6:
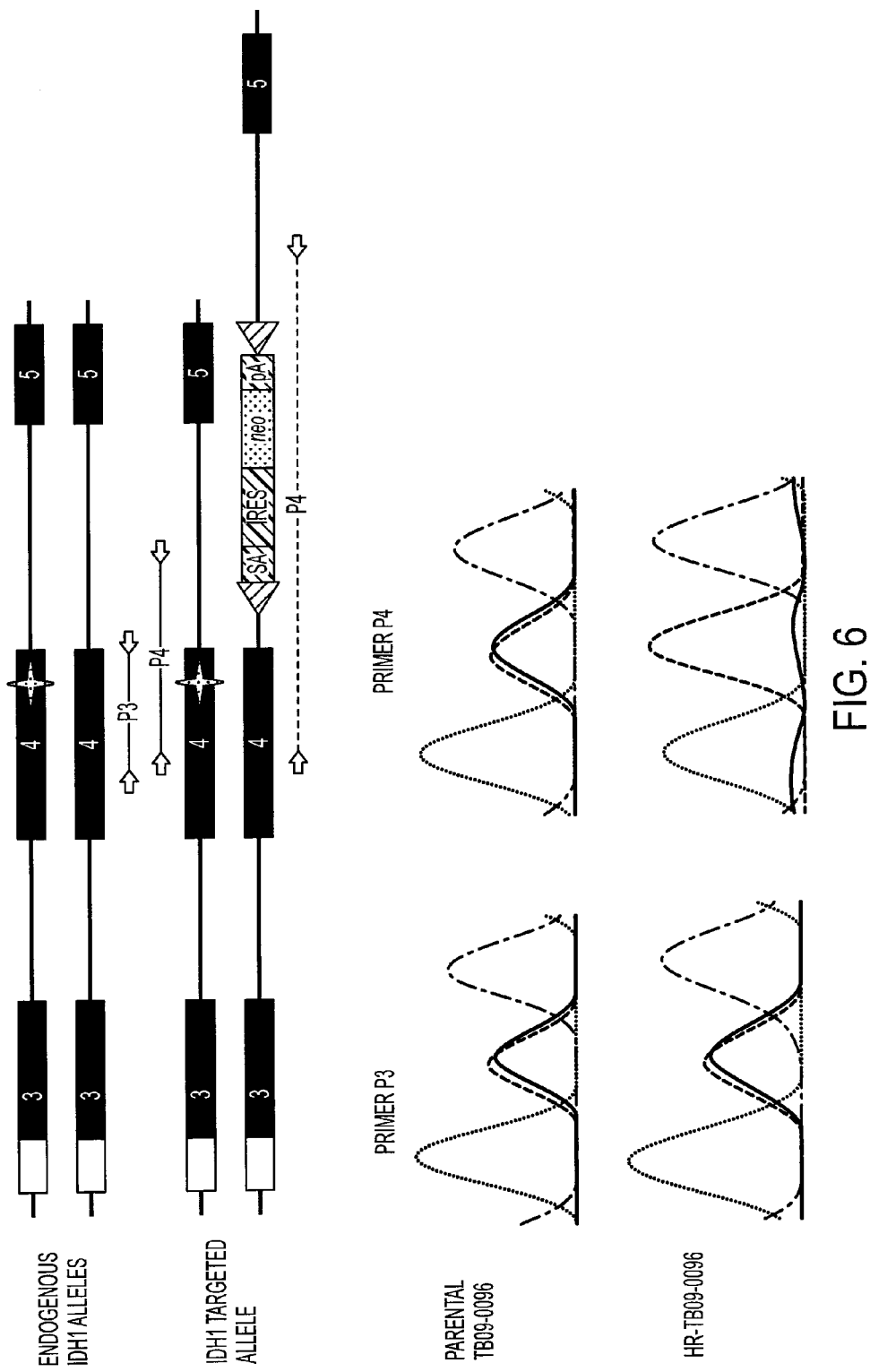
FIG. 6 shows sequencing validation of HR-TB-09-0096 (IDH1R132 homozygous). Sequencing employs two PCR primer pairs, indicated as P3 and P4, that anneal within the LHA element and includes amino acid 132. Both intact and insertion-targeted alleles were sequenced. One primer of primer pair P4 anneals within the LHA element and a second anneals within the RHA element, detecting only intact alleles but not targeted alleles. The sequence data show that the IDH1 WT allele has been targeted by the inserted sequence.
Figure 7:
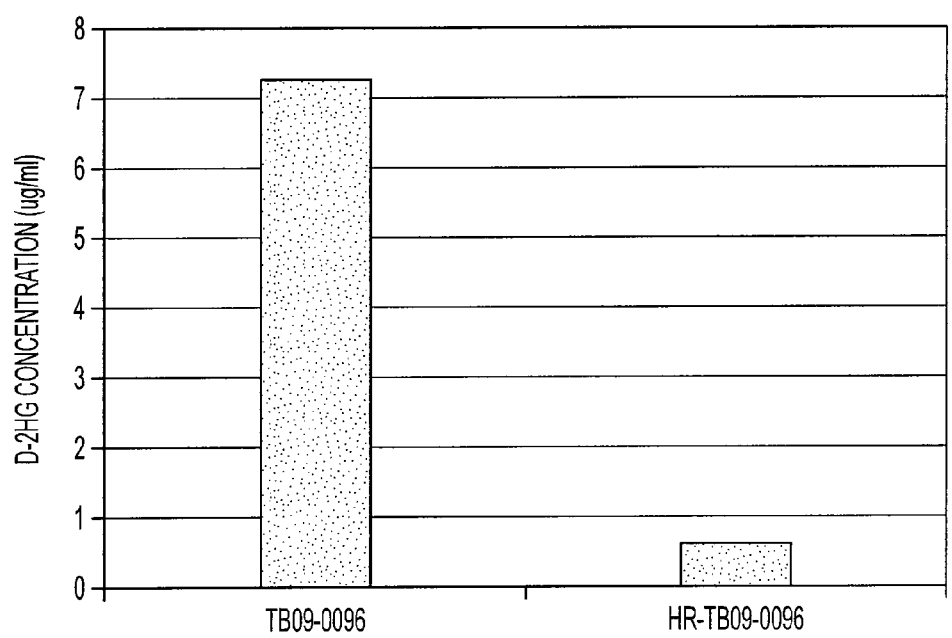
FIG. 7 shows D-2-HG production in TB09-0096 (IDH1R132H heterozygous) and HR-TB-09-0096 (IDH1R132H homozygous). $1 \times 10^6$ cells were plated in 6-well plates and media samples taken after 48 hours.

An anaplastic astrocytoma tissue sample TB09-0096, was dissociated by Liberase™ enzyme (a purified enzyme blend) at 100 ug/ml, and dissociated cells were cultured in stem cell medium. This tumor contains IDH1R132H and TP53G245V mutations. After two and half months culturing (5 passages), cells were transferred to SD medium in a new flask, where growing cells adhered to the flask. Analysis of these cells showed that all contained the original IDH1R132H and TP53G245V mutations (data not shown). After 9 months culturing in SD medium (23 passages), cells were diluted and seeded into 96 well plates. After 5 weeks of growth, single cell colonies were picked and expanded to 6 well plates (FIG. 1). gDNA from different colonies was prepared and the IDH1 gene sequenced (FIG. 2). Most of the colonies were heterozygous for the IDH1R132H mutation. cDNA from these lines and subsequent sequence results showed both the wild-type and mutant (R132H) IDH1 gene was expressed in most TB09-0096 cells derived clones. One colony TB09-0096 (IDH1 WT) displayed IDH1 wild type genotype. It has been previously demonstrated that the IDH1-R132H mutation gives the expressed enzyme the ability to produce D-2-hydroxyglutarate (D-2HG). To determine D-2-HG production in these cells, D-2-HG levels in cell lysates of TB09-0096 (IDH1R132H heterozygous) and TB09-0096 (IDH1 WT) was examined. The TB09-0096 (IDH1R132H heterozygous) cells produced higher D-2HG than the TB09-0096 (IDH1 WT).

Example 2: Generation of the HR-TB09-0096 (IDH1R132H Homozygous) Cell Line

Established standard protocols for gene targeting by homologous recombination with recombinant adeno-associated virus (rAAV) construct. The TB09-0096 (IDH1R132H heterozygous) cell line was used as the parental cell line. Targeting vectors were constructed to introduce IDH1 alleles in the TB09-0096 cell line. An infectious rAAV stock harboring the targeting sequence was generated and applied to the parental cell line, generating cell clones that harbor the rAAV transgenes. A PCR-based method was employed to screen for correct homologous recombinants. Diagnostic PCR primer pairs (designated P1-P2) were used to screen for homologous recombination. The screening approach employs one primer that anneals within the SEPT element and a second primer that is outside the homology region. Homologous recombination was confirmed in 8 clones. These clones were next subjected to sequencing analysis to validate mutation knock-in. The sequence data showed that the IDH1 WT allele was interrupted by the inserted sequence. Next, levels of D-2-HG were measured between the parental cell line and the new clones. The HR-TB096-0096 (IDH1R132H homozygous) cell line produced lower level of D-2HG as compared with the parental cell line TB09-0096 (IDH1R132H heterozygous).

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

We claim:

1. A set of isogenic, continuous human astrocytoma cell lines comprising at least two cell lines comprising:
   (a) an astrocytoma cell whose genome comprises an IDH1 R132H allele and an IDH1 wild-type (WT) allele, and
   (b) an astrocytoma cell whose genome comprises an IDH1 R132H allele and a disrupted IDH1 WT allele, wherein the disruption comprises an insertion of an exogenous synthetic cassette comprising either adeno-associated virus sequences or a neomycin resistance gene, wherein said cell lines grow indefinitely in culture as adherent cells.

2. A kit comprising in a divided container or multiple containers the set of cell lines of claim 1.

3. An isolated and purified, continuous human astrocytoma cell line comprising astrocytoma cells, wherein the genome of the cells comprise an IDH1 R132H allele and a disrupted IDH1 WT allele, wherein the disruption comprises an insertion of a synthetic cassette, wherein said cells grow indefinitely in culture as adherent cells.

4. An isolated and purified, continuous human astrocytoma cell line comprising astrocytoma cells, wherein the genome of the cells comprise an IDH1 R132H allele and a disrupted IDH1 WT allele, wherein the disruption comprises an insertion of adeno-associated virus sequences, wherein said cells grow indefinitely in culture as adherent cells.

5. An isolated and purified, continuous human astrocytoma cell line comprising astrocytoma cells, wherein the genome of the cells comprise an IDH1 R132H allele and a disrupted IDH1 WT allele, wherein the disruption comprises an insertion of a neomycin resistance gene, wherein said cells grow indefinitely in culture as adherent cells.

6. The cell line of claim 3 made by a process comprising:
   (a) enzymatically dissociating an astrocytoma tissue sample to produce dissociated cells,
   (b) culturing the dissociated cells in stem cell medium,
   (c) passaging the dissociated cells in stem cell medium five times,
   (d) transferring the dissociated cells to a flask in a medium, whereby the cells adhere to the flask; and
   (e) isolating the adherent cells in step (d), wherein the adherent cells consist of astrocytoma cells.

7. The cell line of claim 4 made by a process comprising:
   (a) enzymatically dissociating an astrocytoma tissue sample to produce dissociated cells,
   (b) culturing the dissociated cells in stem cell medium,
   (c) passaging the dissociated cells in stem cell medium five times,
   (d) transferring the dissociated cells to a flask in a medium, whereby the cells adhere to the flask; and
   (e) isolating the adherent cells in step (d), wherein the adherent cells consist of astrocytoma cells.

8. The cell line of claim 5 made by a process comprising:
   (a) enzymatically dissociating an astrocytoma tissue sample to produce dissociated cells,
   (b) culturing the dissociated cells in stem cell medium,
   (c) passaging the dissociated cells in stem cell medium five times,
   (d) transferring the dissociated cells to a flask in a medium, whereby the cells adhere to the flask; and
   (e) isolating the adherent cells in step (d), wherein the adherent cells consist of astrocytoma cells.

* * * * *